US008236769B2

(12) United States Patent
Tanaka et al.

(10) Patent No.: US 8,236,769 B2
(45) Date of Patent: *Aug. 7, 2012

(54) AGENT FOR IMPROVING INSULIN RESISTANCE

(75) Inventors: Miyuki Tanaka, Kanagawa (JP); Eriko Misawa, Kanagawa (JP)

(73) Assignee: Morinaga Milk Industry Co., Ltd., Minato-ku, Tokyo (JP)

( * ) Notice: Subject to any disclaimer, the term of this patent is extended or adjusted under 35 U.S.C. 154(b) by 393 days.

This patent is subject to a terminal disclaimer.

(21) Appl. No.: 11/916,008

(22) PCT Filed: Sep. 22, 2006

(86) PCT No.: PCT/JP2006/318809
§ 371 (c)(1),
(2), (4) Date: Nov. 29, 2007

(87) PCT Pub. No.: WO2007/043302
PCT Pub. Date: Apr. 19, 2007

(65) Prior Publication Data
US 2009/0312275 A1    Dec. 17, 2009

(30) Foreign Application Priority Data
Sep. 30, 2005   (JP) ................................. 2005-287884

(51) Int. Cl.
*A61K 31/704*   (2006.01)
*A61P 3/08*   (2006.01)
(52) U.S. Cl. ....................................... 514/26
(58) Field of Classification Search ........................ None
See application file for complete search history.

(56) References Cited

U.S. PATENT DOCUMENTS

| 4,598,069 | A | 7/1986 | Hikino et al. |
| 7,534,770 | B2 | 5/2009 | Higuchi et al. |
| 2003/0207818 | A1 | 11/2003 | Jia et al. |

FOREIGN PATENT DOCUMENTS

| JP | 60-214741 | 10/1985 |
| JP | 07-165587 | 6/1995 |
| JP | 08-012573 | 1/1996 |
| JP | 08-208495 | 8/1996 |
| JP | 10-036283 | 2/1998 |
| JP | 10-298100 | 11/1998 |
| JP | 11-193296 | 7/1999 |
| JP | 2000-319190 | * 11/2000 |
| JP | 2001-240544 | 9/2001 |
| JP | 2001-247473 | 9/2001 |
| JP | 2002-193797 | 7/2002 |
| JP | 2003-286185 | 10/2003 |
| JP | 2005-068132 | 3/2005 |
| WO | WO 03/063894 | 8/2003 |
| WO | WO 2005/094838 | 10/2005 |
| WO | WO 2005/095436 | 10/2005 |
| WO | WO 2006/035525 | 4/2006 |

OTHER PUBLICATIONS

Modan, M. et al., J. Clin. Invest. "Hyperinsulinemia: A Link Between Hypertension Obesity and Glucose Intolerance", vol. 75, pp. 809-817 (1985).*
Shimamoto, et al. "Insulin Resistance and Adult Disease—Hypertension, Diabetes, Hyperlipidemia and Obesity," pp. 1-5, 2003.
Maeda, et al. Basic "Adiponectine," *Adiposcience*, vol. 1, No. 3, pp. 247-257, 2004.
Sartipy, et al. "Monocyte Chemoattractant Protein 1 in Obesity and Insulin Resistance," *Proceedings of the National Academy of Science*, vol. 100, No. 12, pp. 7265-7270, Jun. 10, 2003.
Uysal, et al. "Protection from Obesity-Induced Insulin Resistance in Mice Lacking TNF-α Function," Nature, vol. 389, pp. 610-614, Oct. 9, 1997.
Jazet, et al. "Adipose Tissue as an Endocrine Organ: Impact on Insulin Resistance," *The Netherlands Journal of Medicine*, vol. 61, No. 6, pp. 194-212, Jun. 2003.
Konno, et al. "Effect of 5-campestenone (24-methylcholest-5-en-3-one) on Zucker Diabetic Fatty Rats as a Type 2 Diabetes Mellitus Model," *Hormone Metabolism Research*, vol. 37, pp. 79-83, 2005.
Okyar, et al. "Effect of *Aloe vera* Leaves on Blood Glucose Level in Type I and Type II Diabetic Rat Models," *Phytotherapy Research*, vol. 15, No. 2, pp. 157-161, 2001.
Rajasekaran, et al. "Hypoglycemic Effect of *Aloe vera* Gel on Streptozotocin-Induced Diabetes in Experimental Rats," *Journal of Medicinal Food*, vol. 7, No. 1, pp. 61-66, 2004.
Yongchaiyudha, et al. "Antidiabetic Activity of *Aloe vera* L. Juice I. Clinical Trial in New Cases of Diabetes Mellitus," *Phytomedicine*, vol. 3, No. 3, pp. 241-243, 1996.
Yeh, et al. "Systematic Review of Herbs and Dietary Supplements for Glycemic Control of Diabetes," *Diabetes Care*, vol. 26, No. 4, pp. 1277-1294, 2003.
Panosyan, et al. "Sterols and Sterol Glycosides of Bryonia alba. Khimiya Prirodnykh Soedinenii," No. 3, pp. 353-360, 1977 (no translation).
Tanaka, et al. "Identification of Five Phytosterols from Aloe Vera Gel as Anti-Diabetic Compounds," *Biol. Pharm. Bull.*, vol. 29, No. 7, pp. 1418-1422, 2006.
International Search Report dated Dec. 18, 2006.
Choi, et al. "The Insulin Sensitizing Effect of Homoisoflavone-Enriched Fraction in *Liriope platyphylla* Wang et Tang via PI₃-kinase Pathway," *Life Sciences*, vol. 75, pp. 2653-2664, 2004.

(Continued)

*Primary Examiner* — Shaojia Anna Jiang
*Assistant Examiner* — Bahar Schmidtmann
(74) *Attorney, Agent, or Firm* — Knobbe, Martens, Olson & Bear, LLP

(57) ABSTRACT

To inhibit production of adipocytokines, in particular, adipocytokines that elicit insulin resistance and to prevent onset of pathosis caused by the insulin resistance, or improve the pathosis, the present invention provides an agent or a food or drink which contains 3-O-β-D-glucopyranosyl-4-methylergost-7-en-3-ol, or an organic solvent extract, a hot water extract or a squeezed liquid of a plant of the family Liliaceae or a fraction thereof which contains the compound as an active ingredient.

2 Claims, 1 Drawing Sheet

OTHER PUBLICATIONS

Fukunaga, et al. "Hypoglycemic Effect of the Rhizomes of *Smilax glabra* in Normal and Diabetic Mice," *Biological and Pharmaceutical Bulletin*, vol. 20, No. 1, pp. 44-46, 1997.

Miura, et al. "The Difference in Hypoglycemic Action between Polygonati Rhizoma and Polygonati Officinalis Rhozoma," *Biological and Pharmaceutical Bulletin*, vol. 18, No. 11, pp. 1605-1606, 1995.

Supplementary European Search Report issued to the corresponding European patent application EP 06 81 0422, dated Dec. 7, 2009.

Miura, et al. "The Difference in Hypoglycemic Action between Polygonati Rhizoma and Polygonati Officinalis Phizoma," *Biological and Pharmaceutical Bulletin*, vol. 18, No. 11, pp. 1605-1606, 1995.

* cited by examiner

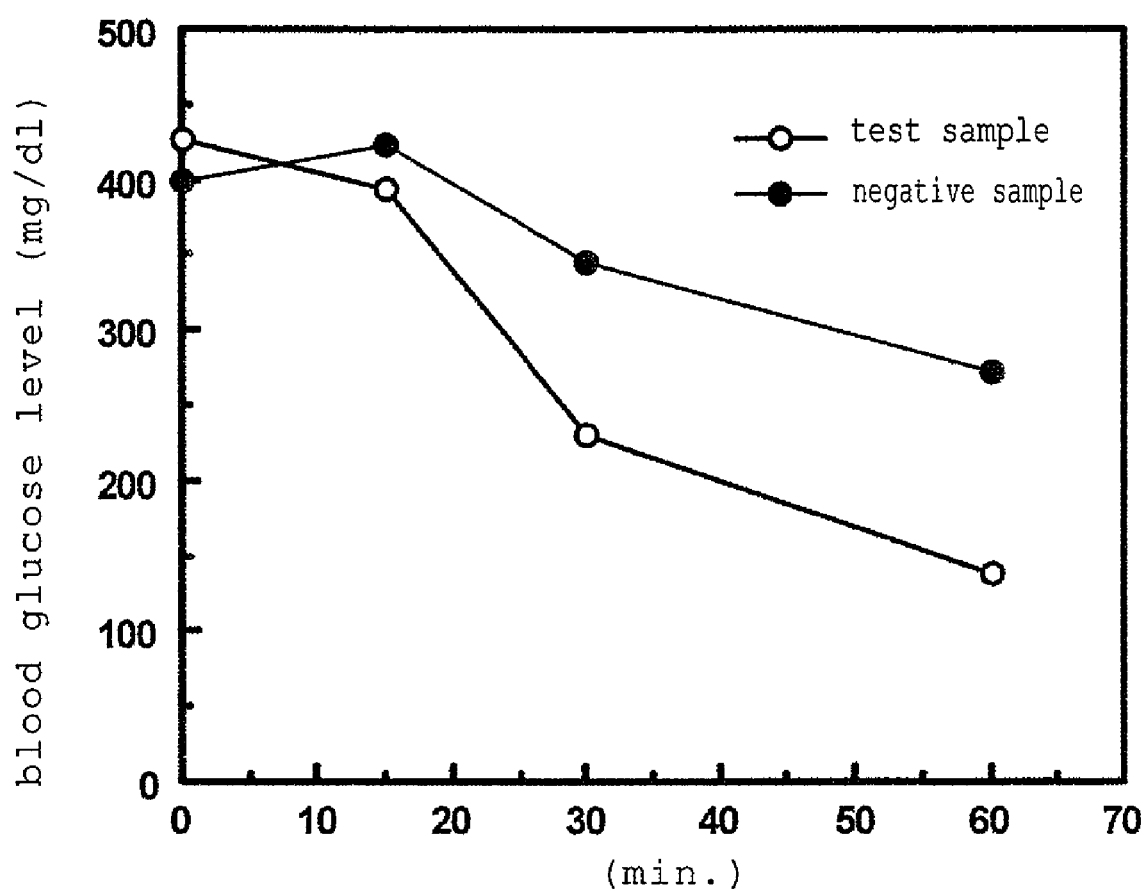

AGENT FOR IMPROVING INSULIN RESISTANCE

CROSS-REFERENCE TO RELATED APPLICATIONS

This application is the U.S. National Phase under 35 U.S.C. §371 of International Application PCT/JP2006/318809, filed Sep. 22, 2006, which was published in a non-English language, which claims priority to JP Application No. 2005-287884, filed Sep. 30, 2005.

TECHNICAL FIELD

The present invention relates to an agent for improving insulin resistance, which contains 3-O-β-D-glucopyranosyl-4-methylergost-7-en-3-ol as an active ingredient, and a food or drink containing the same. In particular, the present invention relates to an agent for improving insulin resistance, which has an effect of controlling production of adipocytokines that are factors involved in onset and exacerbation of pathosis in which the insulin resistance plays a role, such as free fatty acid, plasminogen activator inhibitor, tumor necrosis factor, monocyte chemoattractant protein-1 and resistin, and relates to a food or drink containing the same.

BACKGROUND ART

Insulin is a kind of hormones produced by β cells in Langerhans islets of pancreas, and plays an important role in maintaining homeostasis of living body by affecting lipid metabolism and protein metabolism as well as sugar metabolism via insulin receptors which are present in target tissues of insulin such as skeletal muscles, liver and fats. Examples of the effects of insulin in respective target tissues include promotion of absorption of glucose from blood into muscle cells and adipocytes, promotion of glycogen production in liver and muscle tissues, inhibition of gluconeogenesis in liver, promotion of glucose consumption and fatty acid synthesis in the adipocytes, and inhibition of degradation of lipids.

The insulin resistance means a state that the cells, organs or individuals require larger amounts of insulin than those typically required in order to obtain respective effects of insulin, that is, a state of impaired insulin effects where sensitivity to insulin is decreased. From results of past epidemiologic investigations, hypertension, diabetes, hyperlipidemia (hypertriglyceridemia and hypo-HDL-cholesterolemia), obesity and the like are considered insulin resistance-based pathosis. The insulin resistance causes insufficient effects of insulin in the sugar metabolism, results in compensatory hyperinsulinemia for maintaining blood sugar level, whereby hyperglycemia and glucose intolerance occur and diabetes is promoted by exhaustion of pancreatic β cells. Furthermore, the hyperinsulinemia enhances activation of sympathetic nerves and promotes sodium absorption of kidney to cause hypertension, and also induces postprandial hyperlipidemia and hyperuricemia, an increase in plasminogen activator inhibitor-1 (PAI-1), and the like.

Meanwhile, the insulin resistance induces abnormal lipid metabolism caused by the insufficient effects of insulin, and free fatty acid (FFA) released from adipocytes increases in liver to promote synthesis of triglyceride (TG), resulting in hypertriglyceridemia. Furthermore, activity of lipoprotein lipase (LPL) generally having high insulin sensitivity is decreased in the insulin resistant state, so degradation of TG is decreased and the hypertriglyceridemia is additionally exacerbated. Furthermore, with exacerbation of diabetes, complications such as retinopathy, nephropathy and gangrene caused by angiopathy occur so that cardiac infarction and cerebral infarction that are arteriosclerotic diseases exacerbate, and hypertension exacerbates cardiovascular diseases. As described above, the insulin resistance is considered to be significantly involved in exacerbation of complicated pathosis (Non-patent Document 1).

In recent years, from results of analysis of organ-specific gene expression, it was revealed that various physiologically active substances are secreted from fat tissues, and the fat tissues thus has been recognized to be not only energy storage tissues but also the largest endocrine organ in a living body. Endocrine factors derived from the fat tissues are generically called adipocytokines, and play important roles in maintenance of homeostasis in metabolism. However, it is considered that, in a case of obesity, that is, a state where fats are accumulated, an excessive or a too small amount of adipocytokines are produced and secreted, and the balance of the adipocytokines is disrupted, resulting in insulin resistance.

The adipocytokines are classified into two groups: one that enhances insulin sensitivity; and one that elicits insulin resistance, representative examples of the former group include adiponectin, leptin, AMPK (AMP-dependent protein kinase) and the like. In particular, it has been reported that the adiponectin has an effect of canceling insulin resistance and an effect of inhibiting gluconeogenesis in liver (Non-patent Document 2).

Meanwhile, examples of the adipocytokines that elicit insulin resistance include tumor necrosis factor-α (TNF-α), monocyte chemoattractant protein-1 (MCP-1) that is a kind of inflammatory chemokine, and resistin in addition to the aforementioned FFA and PAI-1. In particular, it has been reported that TNF-α has an effect of eliciting the insulin resistance by inhibiting tyrosine phosphorylation of an insulin receptor and IRSI (insulin receptor substrate 1) in the insulin signal transduction mechanism so that the effect of insulin is attenuated. Furthermore, it has been reported that, in the insulin resistant state, the MCP-1 level in a living body is increased and mRNA of GLUT4 (glucose transporter-4) that is a glucose-transporting carrier, PPARγ (peroxisome proliferator-activated receptors) that is an intranuclear receptor, β3AR (β3-adrenergic receptor) that is a kind of β type catecholamine receptor of an adipocyte, and aP2 (adipocyte fatty-acid-binding protein 2) that is a fatty-acid-binding protein are reduced. Therefore, MCP-1 is considered to be a causative agent of decreasing insulin sensitivity (Non-patent Documents 3, 4 and 5).

As agents for improving insulin resistance, biguanide agents that inhibit gluconeogenesis mainly in liver, and thiazolidine derivatives that improve the insulin sensitivity of muscles and fat tissues have been developed. Those agents have already been permitted as diabetic medicines, and also used for treatment of arteriosclerosis. The thiazolidine derivatives as represented by troglitazone and pioglitazone are each considered to act as a ligand for peroxisome proliferator-activated receptor (PPAR) that is an intranuclear receptor-type transcription factor to promote differentiation of adipocytes, thereby improving insulin resistance.

In addition, an agent for improving insulin resistance containing adiponectin or their genes as an active ingredient (Patent Document 1) a preventive and/or therapeutic agent for diseases caused by insulin resistance containing a substance having affinity to bombesin receptor subtype 3 (BRS-3) as an active ingredient (Patent Document 2), a free fatty acid (FFA) decreasing agent containing a pyrrole derivative as an active ingredient (Patent Document 3) and the like have been disclosed as the agents for improving insulin resistance. Furthermore, a composition for improving insulin resistance containing acetic acid and an ion or salt thereof as an active ingredient (Patent Document 4), an agent for improving insulin resistance comprising a fatty oil containing particular diglyceride and/or monoglyceride (Patent Document 5) and the like have been disclosed as the agents containing a substance derived from a food or drink as an active ingredient.

Plant sterols such as β-sitosterol, campesterol and stigmasterol have been known to have a decreasing effect on blood cholesterol by inhibition of absorption of cholesterol, and practical use thereof has been attempted by adding them as a fat composition to edible oil. Furthermore, an anti-obesity agent and a lipid metabolism-improving agent containing a cholestenone compound as an active ingredient which is synthesized by using plant sterols such as β-sitosterol and campesterol as a starting material have been disclosed (Patent Documents 6 to 8, and Non-patent Document 6).

Furthermore, an adiponectin secretion promoter containing an extract from at least one of rice bran, shimeji mushroom, chrysanthemum, rye, white birch and Spanish Jasmine (*Alpinia zerumbet*), and cycloartane type triterpene or cycloartenol and/or (24S)-24,25-dihydroxycycloartanol which are derivatives of cycloartane type triterpene have been disclosed (Patent Document 9).

The genus *Aloe* belonging to liliaceae plant is a group of plants including *Aloe vera* (*Aloe barbadenisis Miller*), *Aloe arborescens* (*Aloe arborescens Miller var. natalensis Berger*) and the like, and they are empirically known to have various efficacies. For example, immunosuppression improving agents containing a butanol fraction of an aloe extract or a loin (Patent Document 10), an agent related to improving blood glucose levels (Patent Documents 11 to 14), a preventive and improving agent for obesity (Patent Document 15) and the like are disclosed, but the improving effect on insulin resistance of the plants belonging to the genus *Aloe* has not been reported.

[Patent Document 1] International Publication NO. WO2003/63894 pamphlet
[Patent Document 2] Japanese Patent Laid-open NO. 10-298100
[Patent Document 3] Japanese Patent Laid-open NO. 08-12573
[Patent Document 4] Japanese Patent Laid-open NO. 2002-193797
[Patent Document 5] Japanese Patent Laid-open NO. 2001-247473
[Patent Document 6] Japanese Patent Laid-open NO. 07-165587
[Patent Document 7] Japanese Patent Laid-open NO. 11-193296
[Patent Document 8] Japanese Patent Laid-open NO. 2001-240544
[Patent Document 9] Japanese Patent Laid-open NO. 2005-68132
[Patent Document 10] Japanese Patent Laid-open NO. 08-208495
[Patent Document 11] Japanese Patent Laid-open NO. 60-214741
[Patent Document 12] Japanese Patent Laid-open NO. 2003-286185
[Patent Document 13] U.S. Pat. No. 4,598,069
[Patent Document 14] U.S. Patent Application Publication No. 2003/0207818
[Patent Document 15] Japanese Patent Laid-open NO. 2000-319190

[Non-patent Document 1] Insulin resistance and lifestyle-related diseases, Ed. Kazuaki Shimamoto, Shindan to Chiryosha, 2003, pp. 1-5
[Non-patent Document 2] Adiposcience, vol. 1, No. 3, 2004, pp. 247-257
[Non-patent Document 3] Proceedings of the National Academy of Sciences, vol. 100, 2003, pp. 7265-7270
[Non-patent Document 4] Nature, vol. 389, 1997, pp. 610-614
[Non-patent Document 5] The Netherlands Journal of Medicine, vol. 61, NO. 6, 2003, pp. 194-212
[Non-patent Document 6] Hormone Metabolism Research, vol. 37, 2005, pp. 79-83

DISCLOSURE OF THE INVENTION

With use of the biguanide agent that is a conventional drug for improving insulin resistance, gastrointestinal dysfunction or rarely lactic acidosis may occur. Furthermore, a thiazolidine derivative that is the same kind of the agent may sometimes cause severe side effects such as fluid retention, increase in body weight and liver dysfunction, so use thereof requires additional attention. Further, for the insulin resistance in states other than diabetes or hyperglycemia, it has been practically difficult to use antidiabetic agents. Under such circumstances, a development of a functional material which is excellent in safety, can be ingested on a daily basis, and can efficiently improve insulin resistance with as little a pain as possible has been desired.

In view of the aforementioned problems, the inventors of the present invention have studied mechanisms of lifestyle-related disease caused by the insulin resistance, such as hypertension, diabetes, hyperlipidemia (hypertriglyceridemia and hypo-HDL-cholesterolemia) and obesity, and have studied an agent relating to prevention, improvement and the like of the lifestyle-related diseases, that is, an agent for improving insulin resistance. They made attention to adipocytokines that are factors involved in onset and exacerbation of the insulin resistance, and assiduously studied a novel functional material capable of improving insulin resistance by controlling the aforementioned factors. As a result, they found that 3-O-β-D-glucopyranosyl-4-methylergost-7-en-3-ol has an effect for controlling production of adipocytokines such as free fatty acid, TNF-α, and MCP-1 in particular, an efficient effect for decreasing production of adipocytokines that elicits the insulin resistance, thereby the insulin resistance is improved.

Regarding the aforementioned effects of the present invention, Patent Document 9 described only preventive effect of the plant extract on differentiation of cultured adipocytes and a promotion effect of ergosterol on secretion of adiponectin. In addition, it did not describe and disclose that the improving effect of the active ingredient of the present invention on insulin resistance at all.

In addition, the inventors of the present invention found that 3-O-β-D-glucopyranosyl-4-methylergost-7-en-3-ol directly improve the insulin resistance without intervention of insulin secretion property or the like, by investigating using an insulin tolerance test (insulin stress test), in addition to the glucose clamp method, the steady state plasma glucose (SSPG) method and the minimal model method which are conventional methods of evaluating the insulin resistance.

Such an insulin tolerance test is not disclosed in the aforementioned Patent Documents 1 to 5. The inventors of the present invention found a more advantageous effect for improving insulin resistance, which is not affected by insulin secretion property, than conventional effects for improving insulin resistance, and accomplished the present invention.

An object of the present invention is to provide an agent for improving insulin resistance, which contains 3-O-β-D-glucopyranosyl-4-methylergost-7-en-3-ol as an active ingredient. In addition, another object of the present invention is to provide a physiologically functional food or drink containing the agent for improving insulin resistance, such as a food for specified health use.

First invention of the present application to solve the aforementioned problems is an agent for improving insulin resistance containing a compound represented by the following chemical formula (1) as an active ingredient.

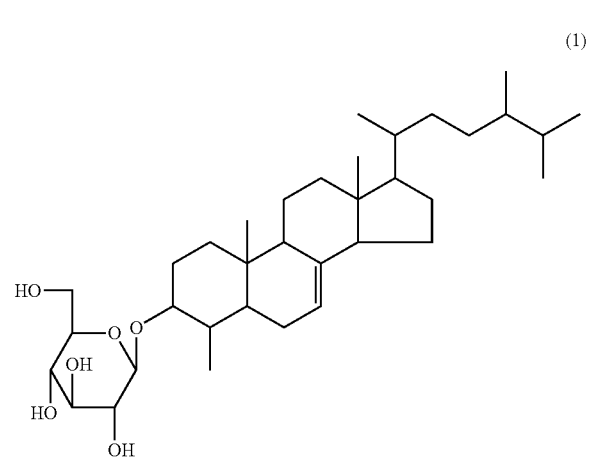

(1)

Second invention of the present application to solve the aforementioned problems is an agent for improving insulin resistance, which contains an organic solvent extract, hot water extract or squeezed liquid of a plant containing a compound represented by the following chemical formula (1), or a fraction thereof as an active ingredient, wherein the organic solvent extract, hot water extract or squeezed liquid of a plant or the fraction thereof contains at least 0.001% by dry mass of a compound represented by the following chemical formula (1). Furthermore, it is preferred that the aforementioned plant is a Liliaceae plant.

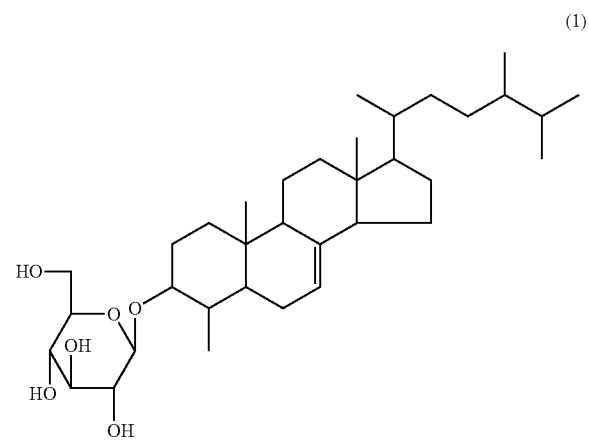

(1)

Third invention of the present application to solve the aforementioned problems is a food or drink containing the agent for improving insulin resistance according to the first or second invention, wherein it is preferred that the food or drink contains 0.0001% by dry mass or more of the compound represented by the aforementioned chemical formula (1).

Fourth invention of the present application to solve the aforementioned problems is use of a compound represented by the aforementioned chemical formula (1), or an organic solvent extract, hot water extract or squeezed liquid of a plant containing at least 0.001% by dry mass of the compound, or a fraction thereof, in the production of an agent for improving insulin resistance. Furthermore, it is preferred that the aforementioned plant is a Liliaceae plant.

Fifth invention of the present application to solve the aforementioned problems is a method for improving insulin resistance, which comprises administering a compound represented by the aforementioned chemical formula (1), or an organic solvent extract, hot water extract or squeezed liquid of a plant containing at least 0.001% by dry mass of the compound, or a fraction thereof, to a subject whose insulin resistance is to be improved. Furthermore, it is preferred that the aforementioned plant is a Liliaceae plant.

The agent for improving insulin resistance of the present invention and the food or drink containing the same can be safely administered or ingested, and have preventive effects on lifestyle-related diseases which is considered to be caused by the insulin resistance. Furthermore, the active ingredient of the agent for improving insulin resistance of the present invention can be produced easily from a plant of the family Liliaceae such as *Aloe vera* (*Aloe barbadensis Miller*) that can be safely ingested from an experiential viewpoint for food and is readily available.

BRIEF DESCRIPTION OF THE DRAWING

FIG. 1 is a graph showing change in blood glucose level in an insulin tolerance test.

BEST MODE FOR CARRYING OUT THE INVENTION

Hereafter, preferred embodiments of the present invention will be explained in detail. However, the present invention is not limited to the following preferred embodiments and can be freely modified within the scope of the present invention. In addition, percentage as used herein indicates mass unless otherwise specified.

In the present invention, the effect of improving insulin resistance (the effect of enhancing insulin sensitivity) means an effect of preventing or improving various adverse effects on health caused by a decrease in insulin sensitivity, such as lifestyle-related diseases. Specifically, the agent of the present invention effectively inhibits an increase or production of adipocytokines that elicit insulin resistance, such as plasminogen activator inhibitor (PAI-1), free fatty acid (FFA), tumor necrosis factor (TNF-α), MCP-1 and resistin, which have preventive and improving effects on pathological conditions involved in the insulin resistance and has an effect on decreasing risks, prevention, improvement or treatment of the diseases involved in the insulin resistance such as hyperinsulinemia, hyperlipidemia, abnormal glucose tolerance, diabetes, hypertension, obesity, arteriosclerosis and the like. Thus, the agent for improving insulin resistance of the present invention can be defined as an agent for enhancing insulin sensitivity or an agent for controlling adipocytokines production, in particular, an agent for controlling production of adipocytokines that elicits insulin resistance.

There are methods for evaluating insulin resistance, such as the glucose clamp method, the steady state plasma glucose (SSPG) method, the minimal model method, the method for evaluating the insulin resistance by calculating homeostasis model assessment insulin resistance (HOMA-IR) from fasting blood glucose level and blood insulin concentration, and the insulin tolerance test. Any of the aforementioned methods can be used for the evaluation of the insulin resistance, however, in the present invention, it is preferred to use the insulin tolerance test (the insulin stress test) using animals, because the test does not affected by insulin secretion property or the like, and thus the insulin sensitivity can be directly investigated.

The compound having a structure represented by the aforementioned chemical formula (1) has an effect of increasing insulin sensitivity, and thus can prevent or improve pathosis caused by insulin resistance. Therefore, the compound can be used as an active ingredient of the agent for improving insulin resistance or a food or drink containing the same. In addition, the insulin sensitivity can also be evaluated by measuring a decrease in blood glucose level after administration of insulin.

The compound used as the active ingredient of the agent for improving insulin resistance (hereinafter also referred to as "the agent of the present invention") of the present invention is the compound having the structure represented by the aforementioned chemical formula (1), that is, 3-O-β-D-glucopyranosyl-4-methylergost-7-en-3-ol. The compound of the present invention has a structure formed by dehydration condensation of the hydroxyl group at the 3-position of 4-methylergost-7-en-3-ol and the hydroxyl group at the 1-position of D-glucose.

It is most preferred that a purity of the compound of the present invention used as the active ingredient of the agent for improving insulin resistance of the present invention is 100%. However, the purity can be appropriately set within a range where the agent has the effect of improving insulin resistance.

Furthermore, the composition used as the active ingredient of the agent for improving insulin resistance of the present invention (hereinafter also referred to as "the composition of the present invention") is an extract of a plant of the family Liliaceae, or a fraction thereof containing at least 0.001% by dry mass, preferably 0.01% by dry mass or more, and more preferably 0.1% by dry mass or more of the aforementioned compound of the present invention. The upper limit of the content of the compound of the present invention is not particularly limited, and it may be, for example, preferably 10% by mass, or 50% by mass, 70% by mass or 90% by mass.

In the present invention, dry mass means a mass measured after a compound is dried by the drying method defined by "Drying Loss Test" that is a general test method as described in Japanese Pharmacopoeia, 14th Revision (Mar. 30, 2001, the Ministry of Health, Labor and Welfare, Ministerial Notification No. 111). For example, the mass of the compound of the present invention can be determined in such a manner that: about 1 g of the compound of the present invention is measured off, and dried at 105° C. for 4 hours; and the resultant is cooled by standing in a desiccator; and the mass of the compound is weighed with scales.

The compound of the present invention or a composition containing the same can be produced by, for example, extracting a fraction containing the compound of the present invention from a plant belonging to the family Liliaceae and containing the compound of the present invention, a part thereof, or a disruption product thereof by using an organic solvent or hot water and concentrating the fraction.

Examples of the aforementioned plant belonging to the family Liliaceae include plants belonging to the genus *Aloe* or *Allium*. Examples of the plants of the genus *Aloe* include *Aloe barbadensis* Miller, *Aloe ferox* Miller, *Aloe africana* Miller, *Aloe arborescen* Miller var. *natalensis* Berger, *Aloe spicata* Baker and so forth. In the production of the compound of the present invention or a composition containing the same, although the whole of the aforementioned plant may be used, it is preferable to use mesophyll (clear gel portion) thereof. Such a plant or a part thereof is disrupted preferably by using a homogenizer or the like and thereby liquefied, and the compound of the present invention or a composition containing the same is extracted from the disruption product by using an organic solvent or hot water. Examples of the organic solvent include alcohols such as methanol, ethanol and butanol and so forth; esters such as methyl acetate, ethyl acetate, propyl acetate and butyl acetate and so forth; ketones such as acetone and methyl isobutyl ketone and so forth; ethers such as diethyl ether and petroleum ether and so forth; hydrocarbons such as hexane, cyclohexane, toluene and benzene and so forth; halogenated hydrocarbons such as carbon tetrachloride, dichloromethane and chloroform and so forth; heterocyclic compounds such as pyridine and so forth; glycols such as ethylene glycol and so forth; polyhydric alcohols such as polyethylene glycol and so forth; nitrile solvents such as acetonitrile and so forth, mixtures of these solvents and so forth. Furthermore, these solvents may be anhydrous or hydrous. Among these solvents, ethyl acetate/butanol mixture (3:1) and chloroform/methanol mixture (2:1) are particularly preferred.

As the extraction method, a method used for usual extraction of a plant component can be used. Usually used is, for example, a method of refluxing 1 to 300 parts by mass of an organic solvent with 1 part by mass of fresh plant or dried plant with heating at a temperature at or below the boiling point of the solvent and stirring or shaking, or a method of performing extraction by ultrasonication at room temperature. By isolating insoluble matters from the extraction liquor using a suitable method such as filtration or centrifugation, a crude extract can be obtained.

The crude extract can be purified by various types of chromatography such as normal or reverse phase silica gel column chromatography. When a gradient of chloroform/methanol mixture is used in normal phase silica gel column chromatography as an elution solvent, the compound of the present invention is eluted with a mixing ratio of chloroform:methanol=about 5:1. Furthermore, when a gradient of methanol/water mixture is used in reverse phase silica gel column chromatography as an elution solvent, the compound of the present invention is eluted with methanol of a concentration of about 95%. The obtained fraction can be further purified by HPLC or the like.

Whether the compound or composition containing the same obtained as described above actually contains the compound of the present invention can be confirmed by measuring the preventive effect of the production of adipocytokines which elicit insulin resistance as an indicator by using, for example, the methods shown in the examples described later. Whether the compound is a glycoside bound with glucose at the aglycon moiety, or whether the aglycon moiety is 4-methylergost-7-en-3-ol can be confirmed by, for example, $^{13}$C-NMR or the like.

The compound of the present invention can also be produced by condensing D-glucose and 4-methylergost-7-en-3-ol. 4-Methylergost-7-en-3-ol can be obtained by extracting from a plant and purifying it. D-Glucose and 4-methylergost-7-en-3-ol can be condensed by, for example, a combination of the methods described in Jikken Kagaku Koza (Lecture of Experimental Chemistry), 4th edition, vol. 26, 1992 (described in p. 272, p. 297 and p. 342). That is, D-glucose is completely acetylated, and then the anomeric position is converted to α-bromide. Then, 4-methylergost-7-en-3-ol is reacted with α-bromide in diethyl ether to attain β-glycosylation, and thereafter the acetyl group is hydrolyzed in a sodium methoxide/methanol mixture to obtain the objective compound.

The compound of the present invention can be used as an active ingredient of the agent for improving insulin resistance of the present invention and a food or drink containing the same as it is. Further, an organic solvent extract, a hot water extract or squeezed liquid of a plant containing the compound of the present invention, or a fraction thereof (hereinafter referred to as "extract etc.") may also be used as an active ingredient of the agent for improving insulin resistance and a food or drink containing the same.

In the present invention, the squeezed liquid can be obtained by processing a homogenate of a plant by a compressor, collecting a crude of squeezed liquid of a plant, and filtering the crude to eliminate insoluble fraction (contaminant) by filter or filter cloth. For example, when the *Aloe vera* is used as a plant of the family Liliaceae, *Aloe vera* squeezed liquid can be prepared by processing mesophyll gel portion obtained by hulling leaf of *Aloe vera* by a crusher, compressing a squeezed liquid to collect *Aloe vera* crude, and filtering the *Aloe vera* crude to eliminate contaminant by filter or filter cloth. In this case, it is preferred that total content of aloin and aloe-emodin, which are contained a lot in leaf-skin of *Aloe vera*, is 5 ppm or less.

The aforementioned extract etc. to be contained in the agent for improving insulin resistance preferably contains at least 0.001% by dry mass, more preferably 0.01 to 1% by dry mass, particularly preferably 0.05 to 1% by dry mass, of the compound of the present invention. Further, the aforementioned extract etc. to be contained in a food or drink preferably contains at least 0.0001% by dry mass, more preferably 0.001 to 1% by dry mass, particularly preferably 0.005 to 1% by dry mass, of the compound of the present invention. Further, the aforementioned extract etc. may be a solution, or can also be lyophilized or spray-dried in a conventional manner and stored or used as powder.

As the agent for improving insulin resistance of the present invention, the compound of the present invention or the composition containing the same such as extract etc. per se, or those combined with a pharmaceutically acceptable carrier can be orally or parenterally administered to a mammal including human. In the drug of the present invention, the compound of the present invention may be a pharmaceutically acceptable salt. Examples of the pharmaceutically acceptable salt include both metal salts (inorganic salts) and organic salts including, for example, those listed in "Remington's Pharmaceutical Sciences," 17th edition, p. 1418, 1985. Specific examples thereof include, but not limited to, inorganic acid salts such as hydrochloride, sulfate, phosphate, diphosphate and hydrobromate, and organic acid salts such as malate, maleate, fumarate, tartarate, succinate, citrate, acetate, lactate, methanesulfonate, p-toluenesulfonate, pamoate, salicylateand stearate. Furthermore, the salt may be a salt with a metal such as sodium, potassium, calcium, magnesium and aluminum or a salt with an amino acid such as lysine. Furthermore, solvates such as hydrates of the aforementioned compound or pharmaceutically acceptable salts thereof also fall within the scope of the present invention.

Dosage form of the agent for improving insulin resistance of the present invention is not particularly limited and can be suitably selected depending on the therapeutic purpose. Specific examples thereof include tablet, pill, powder, solution, suspension, emulsion, granules, capsule, syrup, suppository, injection, ointment, patch, eye drop, nasal drop and so forth. For the preparation, additives generally used in usual agent for improving insulin resistance as pharmaceutical carriers such as excipients, binders, disintegrating agents, lubricants, stabilizers, flavoring agents, diluents, surfactants and solvents for injection and so forth can be used. Further, so long as the effect of the present invention is not degraded, the compound of the present invention, or the extract etc. containing the same can be used in combination with other agents having an effect for improving insulin resistance.

Although the amount of the compound of the present invention or the extract etc. containing the same contained in the agent for improving insulin resistance of the present invention is not particularly limited and can be suitably selected, the amount may be, for example, at least 0.001% by mass, preferably 0.01 to 1% by mass, particularly preferably 0.05 to 1% by mass, in terms of the amount of the compound of the present invention.

The agent for improving insulin resistance of the present invention can prevent, improve or treat various diseases, complications and the like caused by insulin resistance, and can decrease the risks of those diseases, complications and the like. Furthermore, the agent for improving insulin resistance of the present invention can preferably be used for a patient whose insulin resistance is lower than that of a healthy person. In addition, insulin resistance generally means a state where a fasting plasma insulin level is 10 to 15 µU/ml or more, and a HOMA index is 1.73 or more.

Examples of the various diseases caused by insulin resistance include hypertension, hyperlipidemia, diabetes and arteriosclerosis. Examples of the complications caused by the diseases include (a) cerebral stroke, nephrosclerosis and renal failure caused by hypertension, (b) arteriosclerosis and pancreatitis caused by hyperlipidemia, (c) diabetic retinopathy, nephropathy, neuropathy and diabetic gangrene caused by diabetes, and (d) cerebral stroke, cerebral infarction, cardiovascular diseases such as angina pectoris and cardiac infarction, nephropathy such as uremia, nephrosclerosis and renal failure caused by arteriosclerosis. In addition, the inventors of the present invention have found that the compound of the present invention has an effect of decreasing hemoglobin Alc level and improving hyperglycemia (WO 2006/035525). It is preferred that the diseases to which the agent for improving insulin resistance of the present invention is applied are not diseases accompanied with higher hemoglobin Alc levels than that of a healthy person.

Furthermore, an agent of the present invention which has an effect of improving insulin resistance is expected to have an effect of inhibiting production and increase of adipocytokines which elicit insulin resistance, such as TNF-α, MCP-1 and FFA. Therefore, the agent of the present invention has an effect of preventing and/or improving the diseases caused by the increase of the aforementioned adipocytokines which include autoimmune diseases such as rheumatoid arthritis, Crohn's disease, inflammatory diseases in various organs such as nephritis, pancreatitis, hepatitis and pneumonitis, angiopathy, sepsis, cancer cachexia. Thus, the agent for improving insulin resistance of the present invention can preferably be used for a patient in which the production of the adipocytokines is enhanced, in particular, a patient in which the production of the adipocytokines that elicit the insulin resistance is enhanced.

The administration time of the agent of the present invention is not particularly limited and can be suitably selected according to the method for treating an objective disease. Furthermore, the administration route is preferably determined depending on the dosage form, age, sex and other conditions of patients, severity of symptoms of patients and so forth. The dose of the agent of the present invention is suitably selected depending on the dosing regimen, age, sex, severity of disease, other conditions of patients and so forth. The amount of the compound of the present invention as an active ingredient is usually selected from the range of, preferably 0.001 to 50 mg/kg/day, more preferably 0.01 to 1 mg/kg/day, as a tentative dose. Further, when an extract etc. containing the compound of the present invention is used, the dry weight of the extract etc. is selected from the range of, preferably 0.1 to 1000 mg/kg/day, more preferably 1 to 100 mg/kg/day, as a tentative amount. In any case, the dose can be ingested, in a day, once or several times as divided portions.

The compound of the present invention or the composition containing the same can be added to food or drink (a drink or a food) to produce a food or drink having an effect of improving insulin resistance. The form and property of the food or drink are not particularly limited so long as the effect of the active ingredient is not degraded, and the food or drink can be orally ingested, and it can be produced in a conventional manner by using raw materials usually used for food or drink except that the aforementioned active ingredient is added. Furthermore, the amount of the compound of the present invention or the extract etc. containing the same contained in the food or drink of the present invention is not particularly limited and can be suitably selected. For example, the compound of the present invention or the extract etc. containing the same is contained in food or drink in an amount of at least 0.0001% by mass, preferably 0.001 to 1% by mass, more preferably 0.005 to 1% by mass, in terms of the amount of the compound of the present invention.

The food or drink of the present invention can be used for various applications utilizing the effect of improving insulin resistance. For example, it can be used as food or drink useful for decreasing or eliminating risk factors of lifestyle-related diseases caused by insulin resistance. Furthermore, the food or drink of the present invention can prevent the diseases caused by insulin resistance, for example, hypertension, hyperlipidemia, diabetes and the like and can decrease risks of these diseases. Furthermore, the food or drink of the present invention can prevent various complications caused by insulin resistance, for example, cerebral stroke, nephrosclerosis and renal failure caused by hypertension, arteriosclerosis, pancreatitis and the like caused by hyperlipidemia, diabetic retinopathy, nephropathy, neuropathy and diabetic gangrene caused by diabetes, cerebral stroke, cerebral infarction, cardiovascular diseases such as angina pectoris and cardiac infarction, nephropathy such as uremia, nephrosclerosis and renal failure caused by arteriosclerosis, and can decrease risks of these diseases.

Furthermore, the food or drink of the present invention is expected to have an effect of inhibiting production and increase of adipocytokines that elicit insulin resistance, such as TNF-α, MCP-1 and FFA. Therefore, the agent of the present invention has an effect of preventing the diseases and decreasing risks of these diseases caused by the increase of the aforementioned adipocytokines which include autoimmune diseases such as rheumatoid arthritis, Crohn's disease, inflammatory diseases in various organs such as nephritis, pancreatitis, hepatitis and pneumonitis, angiopathy, sepsis, cancer cachexia. Thus, the food or drink of the present invention can preferably be ingested by a patient in which the production of the aforementioned adipocytokines is enhanced, in particular, a patient in which the production of the adipocytokines that elicit insulin resistance is enhanced.

The food or drink of the present invention is preferably marketed as food or drink attached with an indication that the food or drink is used for improving insulin resistance, for example, "food or drink containing a compound having an effect of improving insulin resistance indicated as 'For improving insulin resistance'", "food or drink containing a plant extract indicated as 'For improving insulin resistance'", or "food or drink containing *Aloe vera* extract indicated as 'For improving insulin resistance'" and the like. In addition, because the compound of the present invention, and the composition containing the same have an effect for improving insulin resistance, the indication of "improving insulin resistance" is thus considered to have a meaning of "enhancing insulin sensitivity". Therefore, the food or drink of the present invention can be indicated as "For enhancing insulin sensitivity". In other words, the indication of "For improving insulin resistance" may be replaced by the indication of "For enhancing insulin sensitivity".

The wording used for such an indication as mentioned above is not necessarily be limited to the expression "For improving insulin resistance" or "For enhancing insulin sensitivity", and any other wording expressing the effect for enhancing insulin sensitivity, or the effect for preventing and improving insulin resistance of course falls within the scope of the present invention. As such a wording, for example, an indication based on various uses allowing consumers to recognize the effect for improving insulin resistance or the effect for enhancing insulin sensitivity is also possible. Examples include indication of "Suitable for those who tend to be insulin resistance" and "Useful for decrease or elimination of risk factors (risks) of lifestyle-related diseases".

The aforementioned term "indication" includes all actions for informing consumers the aforementioned use, and any indications reminding or analogizing the aforementioned use fall within the scope of the "indication" of the present invention regardless of purpose, content, objective article, medium etc. of the indication. However, the indication is preferably made with an expression that allows consumers to directly recognize the aforementioned use. Specific examples include actions of indicating the aforementioned use on goods or packages of goods relating to the food or drink of the present invention, actions of assigning, delivering, displaying for the purpose of assigning or delivering or importing such goods or packages of goods indicated with the aforementioned use, displaying or distributing advertisements, price lists or business papers relating the goods with indicating the aforementioned use, or providing information including those as contents with indicating the aforementioned use by an electromagnetic method (Internet etc.) and so forth. The indication is preferably an indication approved by the administration etc. (for example, an indication in a form based on an approval, which is qualified on the basis of any of various legal systems provided by the administration), and it is particularly preferably an indication on advertisement materials at the sales spots such as packages, containers, catalogs, pamphlets and POPs, others documents and so forth.

Examples of the indication further include indications as health food, functional food, enteric nutritive food, food for special dietary uses, food with nutrient function claims, quasi-drug and so forth as well as indications approved by the Ministry of Health, Labor and Welfare, for example, indications approved on the basis of the system of food for specified health uses and similar systems. Examples of the latter include indications as food for specified health uses, indications as food for specified health uses with qualified health claims, indications of influence on body structures and functions, indications of reduction of disease risk claims and so forth, and more precisely, typical examples include indications as food for specified health uses (especially indications of use for health) provided in the enforcement regulations of Health Promotion Law (Japan Ministry of Health, Labor and Welfare, Ministerial ordinance No. 86, Apr. 30, 2003) and similar indications.

The present invention will be explained more specifically with reference to the following examples. However, the scope of the present invention is not limited to the following examples.

First of all, it is explained by Preparation Examples that the compound or composition of the present invention can be produced from a plant belonging to family Liliaceae.

Preparation Example 1

As examples of preparation from a plant belonging to family Liliaceae, examples of preparation of 3-O-β-D-glucopyranosyl-4-methylergost-7-en-3-ol from *Aloe vera* will be described below.

3-O-β-D-Glucopyranosyl-4-methylergost-7-en-3-ol was extracted from *Aloe vera* and purified as described below.

In an amount of 100 kg of mesophyll (clear gel portion) of *Aloe vera* was liquefied by using a homogenizer, added with 100 L of an ethyl acetate/butanol mixture (3:1) and stirred. The mixture was left overnight to separate the ethyl acetate/butanol mixture and the aqueous layer, and the ethyl acetate/butanol mixture was recovered. The extract from this ethyl acetate/butanol mixture obtained by concentrating the ethyl acetate/butanol mixture under reduced pressure weighed 13.5 g. The effect for improving insulin resistance was evaluated for the aforementioned aqueous layer by insulin tolerance test, and the extract from the ethyl acetate/butanol mixture described later in Reference Example 3, and the effect was observed for the extract from the ethyl acetate/butanol mixture. Therefore, it was attempted to isolate and purify components in the extract.

First, the aforementioned extract was examined by thin layer chromatography (Merck Ltd., Silica gel 60F254 and RP-18F2543). As a result, an isolation method based on normal phase silica gel column chromatography using a chloroform/methanol mixture appeared to be suitable. Accordingly, a solution of 13 g of the aforementioned extract dissolved in 1 mL of a chloroform/methanol mixture (1:1) was loaded on a column filled with 400 g of silica gel 60 (Merck Ltd.) to attain adsorption of the components to the column, then the components were eluted with a chloroform/methanol mixture by the stepwise gradient method, in which the methanol concentration was increased stepwise (mixing ratios of chloroform:methanol=100:1, 25:1, 10:1, 5:1 and 1:1), and the eluate was fractionated for each mixing ratio of the aforementioned mixture. The yields of crude purification products obtained from the fractions after removing the solvent were 1.44, 3.0, 1.17, 1.28 and 2.27 g, respectively. It was confirmed by the aforementioned evaluation of improving insulin resistance that, among these fractions, an active component existed in the fraction eluted with the mixture of chloroform:methanol=5:1 (crude purification product A).

Furthermore, to isolate and purify the active component from the aforementioned crude purification product A, this crude purification product A was examined by using thin layer chromatography (Merck Ltd., Silica gel 60F254 and RP-18F2543). As a result, an isolation method based on reverse phase silica gel column chromatography using methanol appeared to be suitable. Accordingly, the aforementioned crude purification product A was dissolved in 1 mL of a chloroform/methanol mixture (1:1) and loaded on a column filled with 180 g of COSMOSIL 140 (Nacalai Tesque, Inc.) to attain adsorption of the component to the column Then, elution was performed by successively using 600 mL of 85% methanol solution, 600 mL of 95% methanol solution and 100 mL of 100% methanol. 3-O-β-D-Glucopyranosyl-4-methylergost-7-en-3-ol was concentrated and isolated in a fraction eluted with 95% methanol and weighed 370 mg after removing the solvent. Hereafter, this product is referred to as compound 1.

Because the compound 1 showed an Rf value very close to that of β-sitosterol glucoside in an examination based on thin layer chromatography, it was anticipated to be a glycoside in which 1 molecule of sugar bound to the aglycon moiety. Furthermore, to examine the sugar composition of the compound 1, the compound 1 was subjected to methanolysis, then made into a TMS derivative and subjected to GC-MS measurement. As a result, in the measurement of the TMS derivative for the sugar portion of the compound 1, it showed main peaks at retention times of 14.28, 14.61 and 16.34 minutes, which were substantially consistent with the retention times of the main peaks of the sample glucose (Nacalai Tesque, Inc.), 14.27, 14.60 and 16.33 minutes. Furthermore, peaks corresponding to the main peaks of the sample galactose (Kishida Chemical Co., Ltd.) and the sample xylose (Kishida Chemical Co., Ltd.) were not observed. Thus, it was confirmed that the type of the sugar contained in the compound 1 was glucose.

From the above results, it was estimated that the compound 1 was a glycoside in which 1 molecule of glucose bound to the aglycon moiety. However, when the compound 1 was measured by $^{13}$C-NMR (125 MHz, CDCl$_3$), the existence of contaminants was confirmed. Therefore, it was considered that further purification should be required to determine its structure. Accordingly, the compound 1 was methanolyzed and then acetylated, and then the structure of the aglycon moiety as well as the binding site of the aglycon moiety and the sugar were confirmed. The method thereof will be described below.

In an amount of 50 mg of the compound 1 was dissolved in methanol (50 mL) containing 5% hydrochloric acid, and the solution was refluxed with heating for 6 hours for methanolysis and dried to obtain a residue (about 30 mg). This residue was purified by silica gel column chromatography (hexane:chloroform=9:1) to obtain a compound 2 (10 mg). This compound 2 (5 mg) was added with acetic anhydride and pyridine (2 drops each) and heated at 70° C. for 30 minutes for acetylation, and then the solvent of the reaction mixture was evaporated to obtain a compound 3. The analysis of the compound 3 was performed by GC-MS and $^{13}$C-NMR (125 MHz, CDCl$_3$).

The results of the analysis of this compound 3 by GC-MS and $^{13}$C-NMR (125 MHz, CDCl$_3$) are shown as follows. 3-Acetoxy-4-methylergost-7-ene used as a reference substance was prepared by extracting from aloe, purifying the extract, confirming the structure of the purified product by $^{13}$C-NMR and acetylating the same.

[$^{13}$C-NMR spectrum (d values, in CDCl$_3$)]; C-1:36.8, C-2:27.3, C-3:78.7, C-4:37.0, C-5:46.9, C-6:26.8, C-7:117.4, C-8:139.4, C-9:49.7, C-10:34.9, C-11:21.6, C-12:39.7, C-13:43.6, C-14:55.1, C-15:23.1, C-16:28.2, C-17:56.3, C-18:12.0, C-19:14.2, C-20:36.5, C-21:19.0, C-22:33.9, C-23:30.6, C-24:39.1, C-25:32.6, C-26:20.4, C-27:18.4, C-28:15.6, C-29:15.3

[GC-MS]
Apparatus: GC-17A/GCMS5050A (SHIMADZU)
GC column: NEUTRA BOND-5 (GL Scienses)
Column temperature: 100° C. (2 min)→(10° C./min)→300° C. (28 min)
Injection temperature: 250° C.
Carrier gas: He (1.3 mL/min)
Interface temperature: 300° C.
MS mode: EI
Ionization energy: 70 eV
[Results]
Reference substance: 3-acetoxy-4-methylergost-7-ene: tR [min]=39.4; m/z 456 [M]$^+$, 441 [M-CH$_3$]$^+$, 396 [M-AcOH]$^+$, 381 [M-CH$_3$—AcOH]$^+$ Compound 3: tR [min]=39.2; m/z 456 [M]⁺, 441 [M-CH₃]⁺, 396 [M-AcOH]⁺, 381 [M-CH₃—AcOH]⁺

The results of the NMR measurement of the compound 3 were consistent with the values of 3-acetoxy-4-methylergost-7-ene shown in a literature (Yukagaku (Oil Chemistry), Vol. 36, No. 5, pp. 301-319, 1987). These results revealed that the compound 2 was 4-methylergost-7-en-3-ol. Furthermore, as a result of FAB-MS measurement, the molecular weight of the compound 1 was found to be 576. When the compound 2 (aglycon moiety) and glucose were condensed, the molecular weight of the obtained compound was 414 (compound 2)+180 (glucose)−18 (water)=576, which was consistent with the molecular weight of the compound 1. The above results revealed that the compound 1 had a structure of 3-O-β-D-glucopyranosyl-4-methylergost-7-en-3-ol.

The molecular formulas, molecular weights and chemical formulas of the compounds are shown below.

(Compound 1)
Molecular formula: $C_{35}H_{60}O_6$
Molecular weight: 576
Chemical formula: The following chemical formula (1)

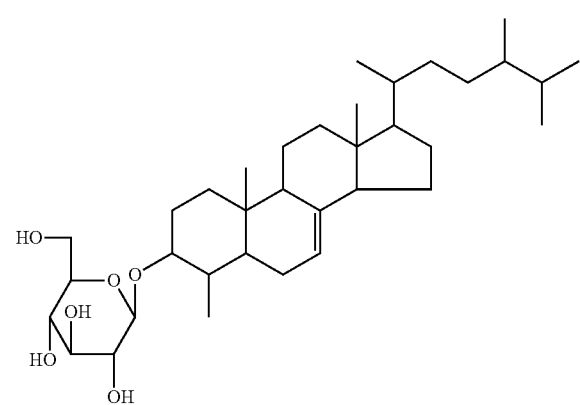

(1)

(Compound 2)
Molecular formula: $C_{29}H_{50}O$
Molecular weight: 414
Chemical formula: The following chemical formula (2)

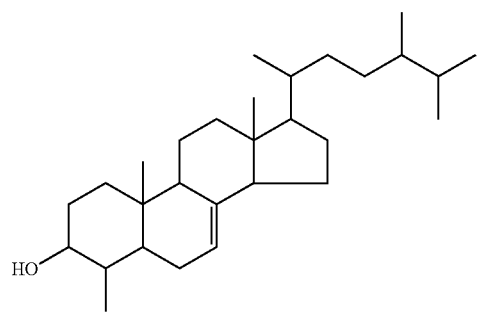

(2)

(Compound 3)
Molecular formula: $C_{31}H_{52}O_2$
Molecular weight: 456

Chemical formula: The following chemical formula (3)

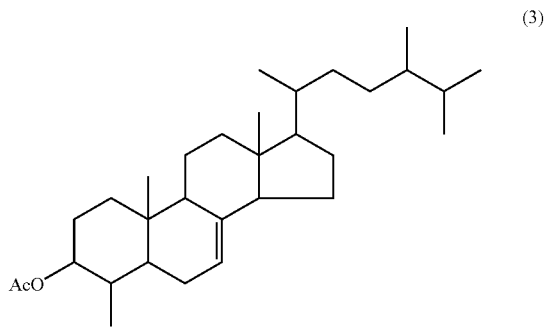

(3)

Preparation Example 2

Mesophyll (clear gel portion) of *Aloe vera* was dried by heating, 0.3 g of disrupted dry *Aloe vera* powder was added with 60 mL of 60, 80 or 100% ethanol, and the mixture was refluxed by heating at 60° C. for 1 hour. The extract was centrifuged at 1500 rpm for 20 minutes, and the supernatant was concentrated under reduced pressure to completely remove ethanol and thereby obtain a crude extract. The dry weights of the crude extracts obtained by extraction using 60, 80 and 100% ethanol were 65, 42 and 18 mg, respectively. It was confirmed by thin layer chromatography that these crude extracts contained 3-O-β-D-glucopyranosyl-4-methylergost-7-en-3-ol.

Preparation Example 3

Mesophyll (clear gel portion) of *Aloe vera* was dried by heating, 0.3 g of disrupted dry *Aloe vera* powder was added with 60 mL of water, and the mixture was refluxed by heating at 95° C. for 5 hours. The extract was centrifuged at 1500 rpm for 20 minutes, and the supernatant was lyophilized to obtain 75 mg of a crude extract. It was confirmed by thin layer chromatography that this crude extract contained 3-O-β-D-glucopyranosyl-4-methylergost-7-en-3-ol.

Preparation Example 4

Mesophyll (clear gel portion) of *Aloe vera* was dried by heating, disrupted and dried, 21 kg of *Aloe vera* powder thus prepared was added with 90 L of a chloroform/methanol mixture (2:1), then immersed overnight in the mixture at room temperature and collected by filtration, and the residue obtained by the filtration was added with 90 L of chloroform/methanol mixture (2:1) again. This procedure was repeated 4 times in total. The obtained filtrate (350 L) was concentrated at 28° C. to finally obtain 784 g of a crude extract. In an amount of 780 g of this crude extract was added with 2 L of a chloroform/methanol mixture (2:1), stirred for 1 hour and filtered to recover the chloroform/methanol mixture layer (A). The residue obtained by the filtration was successively added with 2.5 L of water and 2 L of ethyl acetate and stirred for 1 hour, and the ethyl acetate layer (B) was recovered. The remaining aqueous layer was added with 5 L of chloroform again and stirred for 1 hour, and the chloroform layer (C) was recovered.

The recovered organic solvent extracts A, B and C were mixed, concentrated at 23° C. and loaded on a silica gel column [glass column: 52 mm×350 mm, packed material: IR-63/210-W (Daiso Co., Ltd.)]. Subsequently, while monitoring the eluate by thin layer chromatography, 10 L of a hexane/chloroform mixture (1:1), 10 L of chloroform, 20 L of a chloroform/methanol mixture (10:1) and 20 L of a chloroform/methanol mixture (5:1) were passed through the column in this order, and a fraction 1 (about 1 L), fraction 2 (about 1.5 L), fraction 3 (about 1.5 L) and fraction 4 (about 1.5 L) were recovered in the order of the used elution solvents.

It was confirmed by thin layer chromatography that, among these, the fraction 3 contained the objective glycoside, and then the solvent of the fraction 3 was removed to obtain 131.6 g of a crude extract. In an amount of 130 g of this crude extract was loaded on a silica gel column [glass column: 70 mm×500 mm, packed material: SP-60-40/60 (Daiso Co., Ltd.)] again and eluted successively with 10 L of a chloroform/methanol mixture (30:1), 50 L of a chloroform/methanol mixture (20:1), 10 L of a chloroform/methanol mixture (10:1) and 10 L of a chloroform/methanol mixture (1:1) as elution solvents under conditions of a pressure of 10 kgf·cm$^{-2}$ and a flow rate of 40 mL/min. The eluates were fractionated as 100-mL fractions by using a fraction collector to collect fractions 1 to 8.

The collected fractions were examined by thin layer chromatography, and as a result, it was revealed that the objective glycoside and contaminants existed in the fraction 7. Therefore, this fraction was concentrated, loaded on a silica gel column [glass column: 70 mm×500 mm, packed material: SP-60-40/60 (Daiso Co., Ltd.)] again, and successively eluted with 10 L of a chloroform/methanol mixture (20:1) and 10 L of a chloroform/methanol mixture (10:1) as elution solvents under conditions of a pressure of 10 kgf·cm$^{-2}$ and a flow rate of 40 mL/min. As a result, 25.3 g of 3-O-β-D-glucopyranosyl-4-methylergost-7-en-3-ol was prepared, which was the objective glycoside contained in the fraction eluted with the chloroform/methanol mixture (10:1).

Example 1

This example was performed in order to evaluate a change in the level of free fatty acid (FFA) in the serum caused by an application of the agent of the present invention for improving insulin resistance by using ZDF (Zucker Diabetic Fatty) rats which are model animals for obese diabetes accompanied with insulin resistance.
(1) Preparation of Sample 3-O-β-D-glucopyranosyl-4-methylergost-7-en-3-ol produced in Preparation Example 1 was dissolved in DMSO, and the concentration was adjusted to 15 μg/ml with distilled water to thereby prepare Test Sample. In this case, the final DMSO concentration was adjusted to 0.2%. Furthermore, a solution without the test samples was prepared as a negative sample.
(2) Test Method 6-week-old male ZDF rats (purchased from Charles River Laboratories, Inc., USA) were preliminarily fed with a high-fat diet (Research Diet, Inc.) for 1 month. These rats were divided into groups, each consisting of 6 rats. Each of the groups of rats was orally administered with 1 ml per 400 g of body weight (37.5 μg/kg of body weight) of the Test Sample or the negative sample once a day everyday with a sonde. On the 45th day from the initiation of the administration of the samples, blood was collected from the rats under fasting, and the level of the free fatty acid in serum were measured by using NEFA C-test Wako (Wako Pure Chemical Industries, Ltd.).
(3) Results (Level of Free Fatty Acid in Blood)

Table 1 shows levels of free fatty acid in rats serum at 45th day from the initiation of the administration. As compared with the group administered with the negative sample, it was observed that the free fatty acid levels are decreased to 53% in the group administered with Test sample. During the administration period, no side-effect was observed at all in view of pathological findings. In addition, p values in the tables indicate significance probability by Tukey-Kramer's test.

TABLE 1

| Sample | Free fatty acid (mEq/l) | p value |
|---|---|---|
| Test Sample | 1.948 ± 0.648* | 0.0073 |
| Negative sample | 3.700 ± 0.892 | — |

In the Table, "*" indicates that there was a statistically significant inhibitory effect on the production of free fatty acid.

Example 2

This example was performed in order to evaluate an effect of the agent for improving insulin resistance of the present invention on production quantities of TNF-α and MCP-1 in each cell of adipose tissue by using ZDF (Zucker Diabetic Fatty) rats which are model animals for obese diabetes accompanied with insulin resistance.
(1) Preparation of Samples In Example 2, the same Test Sample and the negative sample as those prepared in Example 1 were used.
(2) Test Method 6-week-old male ZDF rats (purchased from Charles River Laboratories, Inc., USA) were preliminarily fed with a high-fat diet (Research Diet, Inc.) for 1 month. These rats were divided into groups, each consisting of 6 rats. Each of the groups of rats was orally administered with 1 ml per 400 g of body weight (37.5 μg/kg of body weight) of the Test Sample or the negative sample once a day everyday with a sonde. On the 45th day from the initiation of the administration of the samples, epididymal fat tissues were collected from the rats under fasting, and 1 g of each of the fats was added with 1.5 ml of D-MEM/F12 medium containing 0.5% bovine serum albumin, followed by culturing at 37° C. After 1 hour of the culture, culture supernatants were collected, and concentrations of TNF-α and MCP-1 in the culture supernatants were measured by ELISA method (Biosource).
(3) Results (Production Quantities of TNF-α and MCP-1)

Table 2 shows production quantities of TNF-α of adipose tissues. Table 3 shows production quantities of MCP-1 of adipose tissues. As apparent from these results, significant inhibitory effects on the production of both of TNF-α and MCP-1 was observed in the group administered with the Test Sample as compared with the group administered with the negative sample. From the results of the present example, it was revealed that the administration of the agent for improving insulin resistance of the present invention decreases the production of adipocytokines which elicit insulin resistance in the fat tissues that exacerbate the insulin resistance, and prevent the elicit of the insulin resistance. In addition, p values in the tables indicate significance probability by Tukey-Kramer's test.

TABLE 2

| Sample | TNF-α (pg/ml) | p value |
|---|---|---|
| Test Sample | 117.4 ± 47.9* | 0.0298 |
| Negative sample | 353.1 ± 192.8 | — |

In the Table, "*" indicates that there was a statistically significant inhibitory effect on TNF-α production.

TABLE 3

| Sample | MCP-1 (pg/ml) | p value |
| --- | --- | --- |
| Test Sample | 23.3 ± 3.6* | 0.0302 |
| Negative sample | 38.8 ± 14.3 | — |

In the Table, "*" indicates that there was a statistically significant inhibitory effect on MCP-1 production.

Example 3

This example was performed in order to evaluate an enhancing effect of the agent for improving insulin resistance of the present invention on insulin sensitivity by performing an insulin tolerance test using ZDF (Zucker Diabetic Fatty) rats that are model animals for obese diabetes accompanied with insulin resistance.

(1) Preparation of Samples

In Example 3, the same Test Sample and the negative sample as those prepared in Examples 1 and 2 were used.

(2) Test Method 6-week-old male ZDF rats (purchased from Charles River Laboratories, Inc., USA) were preliminarily fed with a high-fat diet (Research Diet, Inc.) for 1 month. The semice were divided into groups, each consisting of 6 rats. Each of the groups of rats was orally administered with 1 ml per 400 g of body weight (37.5 μg/kg of body weight) of the Test Sample or the negative sample once a day everyday with a sonde. On the 35th day from the initiation of the administration of the samples, an insulin tolerance test was performed. In the present example, the insulin tolerance test was performed in such a manner that: the rats were fasted for 4 hours, and were then intraperitoneally administered with 10 U/Kg of body weight of a human insulin (Eli Lily and Company); and changes with time in blood glucose level were measured from the initiation of the administration of the insulin to after 60 minutes later.

(3) Results (Insulin Tolerance Test)

The results of the present example were as shown in FIG. 1. FIG. 1 shows the results of the insulin tolerance test. As apparent from FIG. 1, the group administered with the Test sample exhibited lower blood glucose levels than those of the group administered with the negative sample at any time points from 15 minutes to 60 minutes after the initiation of the administration of insulin. From the results of the present example, it was revealed that the administration of the agent for improving insulin resistance of the present invention enhances the insulin sensitivity.

INDUSTRIAL APPLICABILITY

The present invention can provide an agent for improving insulin resistance which is safe without side effects and is capable of enhancing insulin sensitivity, and can provide the physiologically functional food or drink such as foods for specified health use containing the agent for improving insulin resistance. The agent for improving insulin resistance and the physiologically functional food or drink containing the agent for improving insulin resistance have improving or preventive effects on diseases, complications and the like caused by a decrease insulin sensitivity, for example the lifestyle-related diseases such as hypertension, diabetes, hyperlipidemia and arteriosclerosis, and have decreasing effects on risks of those diseases, complications and the like.

What is claimed is:

1. A method for treating hyperinsulinemia or abnormal glucose tolerance in a mammal in need thereof, which comprises administering a purified compound represented by the following formula (1) at 0.001% to 1% by dry mass, to said mammal in need thereof, wherein the compound is obtained from a chloroform and methanol (2:1) mixture extract of mesophyll of *Aloe barbadensis Miller* or *Aloe arborescen Miller* var. *natalensis Berger*, or a fraction thereof comprising the compound

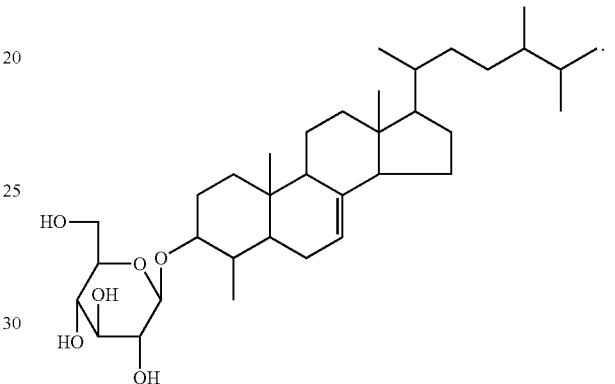

(1)

2. A method for treating hyperinsulinemia or abnormal glucose tolerance in a mammal in need thereof, which comprises administering a purified compound represented by the following chemical formula (I) at 0.001% to 1% by mass to the mammal in need thereof

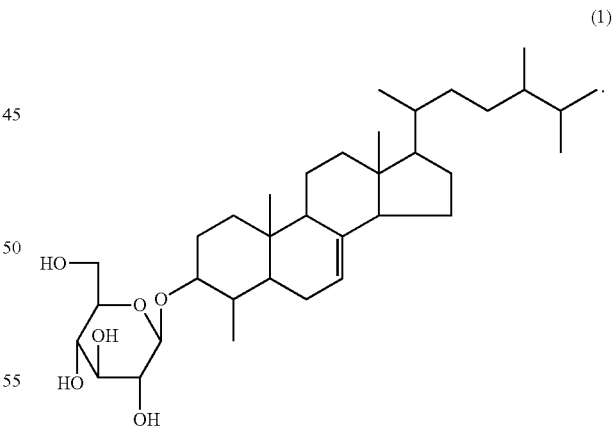

(1)

* * * * *